United States Patent [19]

Mazanec et al.

[11] Patent Number: 4,608,447
[45] Date of Patent: Aug. 26, 1986

[54] PROCESS FOR THE PRODUCTION OF ALCOHOLS

[75] Inventors: Terry J. Mazanec, Solon; Gary V. Goeden, North Royalton; John G. Frye, Jr., Solon, all of Ohio

[73] Assignee: The Standard Oil Company, Cleveland, Ohio

[21] Appl. No.: 707,270

[22] Filed: Mar. 1, 1985

[51] Int. Cl.$^4$ .................. C07C 29/00; C07C 31/08
[52] U.S. Cl. ................................ 568/902; 502/344
[58] Field of Search ........................... 568/902 H

[56] References Cited

U.S. PATENT DOCUMENTS

| | | | |
|---|---|---|---|
| 1,562,480 | 11/1925 | Wietzel et al. | 568/905 |
| 2,773,895 | 12/1956 | Ballard et al. | 260/491 |
| 3,536,632 | 10/1970 | Kroll | 252/430 |
| 4,346,179 | 8/1982 | Sugier et al. | 568/902 |
| 4,400,561 | 8/1983 | Mitchell et al. | 568/902 |
| 4,405,815 | 9/1983 | Keim et al. | 568/902 |

Primary Examiner—J. E. Evans
Attorney, Agent, or Firm—Salvatore P. Pace; David J. Untener; Larry W. Evans

[57] ABSTRACT

Methanol is converted into alcohols containing at least two carbon atoms by reaction with hydrogen and/or carbon monoxide at elevated temperature and superatmospheric pressure in the presence, as catalyst, of (i) an oxide of Th and/or U and (ii) one or more alkali metals the latter being present in an amount of at least 1% by weight. Preferably the catalyst is free of hydrogenating metals. The methanol can be prepared by reaction of hydrogen and carbon monoxide in the presence of a methanol-forming catalyst.

17 Claims, No Drawings

PROCESS FOR THE PRODUCTION OF ALCOHOLS

BACKGROUND OF THE INVENTION

1. Field of the Invention

This invention relates to a process for the production of alcohols, more particularly to a process for the production of alcohols containing at least two carbon atoms from methanol, a process which is sometimes referred to as homologation, using a catalyst containing an oxide or uranium and/or thorium.

There are several processes available for the production of methanol from natural gas or from synthesis gas and it is probable that methanol will be produced and traded in increasing quantities in the near to medium term future. However, there is a need for alcohols containing two and more carbon atoms for use such as solvents, gasoline additives and chemical intermediates for a wide range of products. It is therefore an object of the present invention to provide a process for converting methanol into $C_2$ and higher alcohols.

2. Description of Art

U.S. Pat. No. 1,562,480 describes the reaction of methanol with carbon monoxide to produce higher molecular weight compounds such as alcohols and aldehydes using a catalyst. The catalysts described contain a combination of metals and can contain hydrogenating metal constituent and a hydrating metal constituent. As examples of hydrogenating constituents are mentioned copper, silver, gold, tin, lead, antimony, bismuth, zinc, cadmium and thallium and as examples of the hydrating constituent are mentioned oxides of titanium, thorium, vanadium, niobium, manganese, cerium, lanthanum, tantalum, chromium, molybdenum, tungsten, uranium, didymium, glucinium and aluminum. The catalyst can have added alkali or alkaline earth metal compounds which are reported to be sometimes helpful in increasing the efficiency.

Further, U.S. Pat. No. 1,996,101 describes the reaction of methanol with carbon monoxide and hydrogen using an iron or cobalt-containing catalyst in which the iron or cobalt is present in an acid radical such as a ferrate or ferrite of an alkali or alkaline earth metal.

More recently the homologation of methanol using a homogeneous catalyst has been previously described, in particular catalysts containing cobalt and ruthenium optionally together with a phosphine and iodide have been disclosed.

For example, U.S. Pat. No. 4,126,752 describes a process for the conversion of methanol to ethanol in which the methanol is reacted with water in the liquid state and carbon monoxide using a Group VIII metal catalyst and a water soluble basic inorganic compound such as an oxide, hydroxide carbonate or bicarbonate of an alkali metal.

U.S. Pat. No. 4,405,815 describes a process for production of ethanol and acetaldehyde from methanol by reaction of the methanol with hydrogen and carbon monoxide using a catalyst system containing cobalt and an iodide promoter and a polydentate ligand such as phosphine.

U.S. Pat. No. 4,423,258 describes the conversion of methanol to ethanol by reaction with hydrogen and carbon monoxide in an inert solvent and using as catalyst a cobalt compound, a manganese compound and a tertiary phosphine.

The present invention provides an improved process using a heterogeneous catalyst for the conversion of methanol to alcohols containing at least two carbon atoms.

SUMMARY OF THE INVENTION

According to one aspect of the present invention, a process for the conversion of methanol to alcohols containing at least two carbon atoms comprises reacting methanol with carbon monoxide and/or hydrogen in the presence of catalyst containing (i) an oxide of Th and/or U and (ii) one or more alkali metals, the latter being present in an amount at least 1% by weight of alkali metal based on the total weight of metal oxide and alkali metal.

According to a further aspect of the present invention, a process for the conversion of methanol to alcohols containing at least two carbon atoms comprises reacting methanol at elevated temperature and pressure with at least one gas selected from the group consisting of carbon monoxide and hydrogen in the presence of a catalyst containing an oxide of a metal selected from the group consisting of Th and U which catalyst is free of hydrogenating metals.

DETAILED DESCRIPTION OF THE INVENTION

The amount of alkali metal in the catalyst is at least 1 percent, preferably at least 3%, more preferably at least 5%. While there is no upper limit on the amount of alkali metal it is not convenient to exceed 20%. A convenient range is therefore 3 to 20%.

It has been found, unexpectedly, that the presence of a hydrogenating metal reduces the effectiveness of the catalyst.

Preferably therefore the catalyst is free of hydrogenating metals, for example, copper and zinc. By "free of hydrogenating metals" is meant that such metals are either absent or, if present, are only present as impurities in amounts that arise by preparing the catalyst from ordinary commercially available materials.

The catalyst can be formed into pellets with a binder such as graphite which can suitably be used in an amount from 1 to 10% by weight.

Preferably the catalyst consists essentially of the metal oxide and the alkali metal. More preferably the catalyst consists of the metal oxide and the alkali metal. In either case the binder can be present.

The preferred metal oxide is thorium oxide ($ThO_2$) and a particularly preferred combination of metals is thorium and cesium, optionally together with potassium.

The catalyst can be prepared by precipitation of the thorium or uranium oxide, hydroxide or carbonate from aqueous solution with, for example, potassium hydroxide. The precipitate is separated, washed to remove excess potassium, dried and calcined. To incorporate cesium the washed precipitate can be impregnated with a solution of a cesium compound and then calcined.

The process for the conversion of methanol to alcohols containing at least two carbon atoms is conveniently effected at 100° to 600° C. preferably 250° to 500° C. most preferably 325° to 425° C.

The space velocity is suitably from 1 to 100,000, preferably from 1000 to 10,000 volumes of gas per volume of catalyst per hour.

The pressure can be from 10 to 2500 psig preferably 50 to 2000 psig.

The feed to the process can be pure methanol or can be a mixture containing methanol in a major or minor amount preferably with synthesis gas. A preferred feed is one consisting essentially of methanol and synthesis gas. Preferably the synthesis gas has a molar ratio of $CO/H_2$ of 0 to 10.0 to 1 more preferably from 0.3 to 3.0 to 1.

It is preferred that other components in the feed such as steam, carbon dioxide and air do not exceed 10% by volume, and are preferably less than 5%.

SPECIFIC EMBODIMENTS

The invention is illustrated by the following examples.

Catalyst Preparations

Preparation (A): Catalyst Containing Thorium and Potassium 200 g of $Th(NO_3)_4.4H_2O$ was dissolved in 2 liters of water, heated to 90° C. and precipitated by the addition of a 2 Molar solution of potassium carbonate ($K_2CO_3$) while stirring. The pH was raised to 7.5 and then the mixture stirred for 2 hours while cooling. The pH was reduced to 5.6 by the addition of 2 Molar nitric acid. The white solid was collected by filtration on a Buchner funnel and washed with 500 cc of distilled water without allowing it to dry. The solid was then evacuated to dryness and further dried at 120° C. for 70 hours and then calcined at 400° C. for 4 hours to convert to the oxide and remove thermally decomposable components. It was crushed and sieved to 10–30 mesh. Analysis of the material was as follows:

Th 61% by weight
K 12% by weight corresponding to a formula of $ThK_{1.17}O_x$.

Preparation B: Catalyst Containing Thorium and Potassium and (C) Catalyst Containing Thorium, Cesium and Potassium Preparation (B) 200 g of $Th(NO_3)_4.4H_2O$ were dissolved in 2 liters of absolute methanol at room temperature. Enough 2 Molar potassium hydroxide in methanol was then added dropwise to the rapidly stirred nitrate solution to bring the pH to 7.0. The precipitate was then filtered and washed 3 times with one liter portions of absolute methanol by alternately reslurrying and filtering. The washed precipitate was then dried overnight at 110° C. in a drying oven, then calcined in air up to 400° C. using a temperature programmed calcination. The calcined precipitate was then water washed by stirring with one liter of distilled water for 2 hours, and then completely powdered and vacuum filtered on a medium glass frit. The solid was further water washed while on the frit with 3–100 cc portions of distilled water. The washed material was then dried overnight at 110° C. This catalyst contained less than 0.1% by weight of K. One half of the material was pelletized with 3% by weight of graphite and was then used in Examples 6 to 8.

Preparation C

The other half was impregnated with a solution of cesium hydroxide and redried to give a material containing 2% by weight of cesium. This material was then pelletized with 3% by weight of graphite.

Preparation D: Catalyst Containing Thorium, Potassium and Cesium

The procedure described in Preparation B was repeated to the stage of calcination, water washing and drying. 47.07 g of the material thus prepared were impregnated with 25 cc of a solution prepared by dissolving 4.917 g of 81.4% CsOH in distilled water up to 25 cc of total volume. The impregnated material was dried overnight at 110° C. then pelletized with 3% weight of graphite and sieved to a 10–30 mesh fraction. The resulting catalyst contained 7% by weight of cesium.

Preparation E: Catalyst Containing Uranium, Cesium and Potassium 250 g of $UO_2(NO_3)_2.6H_2O$ were dissolved in 2 liters of room temperature absolute MeOH. While stirring the solution vigorously with a mechanical stirrer a 2 Molar KOH/MeOH solution was added (rapid dropwise addition) until the pH of the mixture was 7.0. The precipitate (light yellow in color) was vacuum filtered then washed once by reslurrying with 2 liters of MeOH and refiltering. The material was then dried overnight at 110° C. in a drying oven (material was still yellow after drying) and then calcined up to 400° C. in air using the temperature programmed calcination described earlier. The calcined material was orange in color. This material was then water washed by stirring with about one liter of distilled water for about 2 hours. The solid was completely powdered and still orange in color following the washing. The solid was then vacuum filtered with a medium glass frit and additionally washed with 3–50 ml portions of distilled water while still on the frit. The washed solid was then dried overnight at 110° C. A portion of the above material (50.02 g) was impregnated with 30 cc of a CsOH solution (made by dissolving 5.21 g of 81.4% CsOH in enough distilled water to make 30 cc total volume). The impregnated material was then dried for 4 hours at 110° C., then pelletized with 3% by weight of graphite. The resulting catalyst pellets were sieved to a 10–30 mesh fraction. The catalyst contained 7% by weight of cesium and less than 0.1% by weight of potassium.

Preparation F: Catalyst Containing Thorium and Potassium

Preparation B was repeated except 400.0 g of $Th(NO_3)_4.4H_2O$ in 3 liters of absolute methanol was used as far as the water washing and drying step. A 50.0 g sample of the dried material was impregnated with 13.1 ml of 2 molar KOH in water to give a material containing 2.0% by weight of potassium. A 1.5 g portion of graphite was added and dried at 120° C. overnight. The material was pelletized and crushed to give a 10–30 mesh fraction.

Preparation G: Alcohol Synthesis Catalyst Containing Copper and Thorium 150.0 g of $Th(NO_3)_4.4H_2O$ and 100 g of $Cu(NO_3)_2.2\frac{1}{2}H_2O$ were dissolved in 2 liters of distilled water. A 2 Molar solution of potassium carbonate was added to the mixture over a period of about $\frac{1}{2}$ hour until the pH reached 9.5. The pH was then adjusted to 7.0 by adding 2 molar nitric acid. The mixture was then vacuum filtered and the filter cake reslurried with 1 liter of distilled water and again vacuum filtered. This procedure was repeated and the filter cake dried overnight at 120°

C. The dried material was calcined as follows: from 20° C. to 400° C. over 10 hours, then at 400° C. for 2 hours and allowed to cool to room temperature. The material was then ground to a fine powder, 3% by weight of graphite added, pelletized and the pellets crushed and sieved to 10 to 30 mesh.

Examples using thorium based catalysts.

EXAMPLES 1-4 AND EXPERIMENT A

Methanol homologation experiments were performed and the results are summarized in the following Table 1. Experiment A and Examples 1 to 4 consisted of feeding synthesis gas at 1000 psig to two reactors in series. The first reactor was employed to convert the synthesis gas to a mixture containing methanol together with hydrogen and carbon monoxide. The first reactor contained as methanol synthesis catalyst $Cu_{1.5}$—Th—$K_x$—$O_y$ prepared as described in Preparation G above. The second reactor which was employed to convert the methanol to higher alcohols contained the non-pelletized catalyst of this invention prepared in Preparation A. The products from Experiment A at 250° C. were identical with those obtained without the second reactor in place thus showing that no reaction had taken place. The feed to the second reactor consisted of:

(i) 1875 liters/liter/hour of a gas consisting of 52% $H_2$ and 48% CO and (ii) 0.2 g/cc/hour of a liquid consisting of 89% $CH_3OH$ and 5.9% $C_2$ and higher alcohols.

Experiment A and Examples 1 to 4 show that with increasing temperature both the percentage of higher alcohols and the percentage of methanol converted to higher alcohols increase. The reason for the fact that no methanol was converted in Experiment A was that the temperature was too low for the particular space velocity, pressure and catalyst employed.

TABLE 1

Methanol Homologation Results Over $ThK_xO_y$

| Catalyst | Example No. | Temp (°C.) | CO Conversion %* | % Higher Alcs | % MeOH Conv. to Hi Alcs** |
|---|---|---|---|---|---|
| $ThK_xO_y$ of Preparation A | Exp. A | 250 | 27.0 | 5.9 | 0.0 |
| | 1 | 325 | 27.3 | 6.9 | 0.8 |
| | 2 | 350 | 24.4 | 7.3 | 1.4 |
| | 3 | 375 | 29.8 | 11.5 | 6.7 |
| | 4 | 400 | 33.3 | 17.2 | 12.3 |

*% CO Conversion = 100 × (Moles CO fed − Moles CO recovered)/Moles CO fed
**% MeOH converted to higher alcohols is equal to 100 × (moles of carbon in higher alcohols at the temperature concerned less moles of carbon in higher alcohols at 250° C.) divided by (moles of methanol at 250° C.)

The results in Table 1 demonstrate the conversion of methanol within a mixture of alcohols to higher alcohols and that over the range 325° to 400° C. conversion is favored by higher temperatures.

EXAMPLES 6 TO 16

Further examples were carried out using a feed of synthesis gas of molar ratio of $CO/H_2$ of 1:1 and methanol over a preheated bed of glass beads at 250° C. and into the catalyst bed at the desired temperature. In each case the pressure was 1000 psig and the feed rate was 2400 liters/liter/hour of gas and 0.5-1.0 g/cc/hr of liquid feed.

The catalyst used in Examples 6 to 8 was prepared in Preparation B and was pelletized, and that in Examples 9 to 13 was prepared in Preparation C.

The catalyst used in Examples 14 to 16 was that prepared in Preparation D (pelletized).

TABLE 2

Methanol Homologation Experiments Over Cs-Doped $ThK_xO_y$ (amount of K less than 0.1% by weight)

| Example No. | % Cs | Temperature °C. | Methanol Converted, %* | % MeOH Conv to Hi Alcs** |
|---|---|---|---|---|
| 6 | 0 | 350 | 64.7 | 2.0 |
| 7 | | 375 | 78.9 | 3.2 |
| 8 | | 400 | 97.4 | 2.3 |
| 9 | 2 | 350 | 38.2 | 2.8 |
| 10 | | 375 | 72.3 | 6.4 |
| 11 | | 400 | 92.8 | 8.4 |
| 12 | | 425 | 98.6 | 4.8 |
| 13 | | 450 | 98.8 | 5.2 |
| 14 | 7 | 375 | 40.8 | 16.3 |
| 15 | | 400 | 74.4 | 22.4 |
| 16 | | 425 | 94.2 | 12.6 |

*% Methanol Converted = 100 × (MeOH fed − MeOH recovered)/MeOH fed
**% Methanol Converted to Higher Alcohols = 100 × (moles of C in Higher Alcohols/moles MeOH fed)

These examples illustrate that increasing the % of cesium in the catalyst results in an increasing % conversion of methanol to higher alcohols.

The following tables show the effects of liquid flow rates, $H_2/CO$ ratio, and gas flow rates on the methanol homologation yields. The conditions are as indicated in the tables.

The catalyst used in Examples 17 to 39 was prepared in Preparation D (pelletized).

TABLE 3

The Effect of Liquid Flow Rates and Temperature on Methanol Homologation Over 7% $Cs/ThO_2$

| Example No. | MeOH Rate g/hr | Temperature °C. | MeOH Conv % | % MeOH Coverted to Higher Alcohols |
|---|---|---|---|---|
| 17 | 4.270 | 375 | 60.73 | 14.0 |
| 18 | 7.600 | 375 | 40.79 | 16.3 |
| 19 | 20.260 | 375 | 20.70 | 5.2 |
| 20 | 4.270 | 400 | 88.70 | 21.0 |
| 21 | 7.123 | 400 | 74.40 | 22.4 |
| 22 | 21.840 | 400 | 47.45 | 7.8 |
| 23 | 3.800 | 425 | 87.50 | 17.4 |
| 24 | 9.260 | 425 | 94.20 | 12.7 |
| 25 | 25.250 | 425 | 83.60 | 2.4 |

All examples at 1000 psig, 1:1 $H_2$:CO, 0.8 SLPM 18 mls catalyst used.

TABLE 4

The Effect of $H_2/CO$ Ratio on Methanol Homologation Over 7% $Cs/ThO_2$

| Example No. | MeOH Rate g/hr | $H_2$:CO -SLPM- | Temp. °C. | MeOH Conv % | % MeOH Conv. to Higher Alcs. |
|---|---|---|---|---|---|
| 26 | 12.35 | 0.4/0.8 | 400 | 81.80 | 8.8 |
| 27 | 12.35 | 0.8/0.4 | 400 | 77.72 | 5.6 |
| 28 | 12.27 | 1.2/0.4 | 400 | 59.30 | 11.2 |
| 29 | 8.55 | 0.8/0.0 | 400 | 33.9 | 11.8 |
| 30 | 8.55 | 0.6/0.2 | 400 | 40.7 | 11.1 |
| 31 | 8.55 | 0.4/0.4 | 400 | 54.0 | 12.7 |
| 32 | 8.55 | 0.2/0.6 | 400 | 62.8 | 7.5 |
| 33 | 8.55 | 0.0/0.8 | 400 | 79.2 | 4.2 |

All examples at 1000 psig, 18 mls of catalyst used.

TABLE 5
The Effect of Gas Flow Rate On Methanol Homologation Over 7% Cs/ThO$_2$

| Example No. | MeOH Rate g/hr | H$_2$ + CO -SLPM- | Space Velocity v/v/hour | Temp. °C. | MeOH Conv % | % MeOH Conv to Higher Alcs. |
|---|---|---|---|---|---|---|
| 34 | 7.60 | 0.40 | 1333 | 400 | 61.95 | 8.05 |
| 35 | 8.55 | 0.80 | 2666 | 400 | 50.50 | 9.63 |
| 36 | 7.60 | 1.50 | 5000 | 400 | 70.03 | 8.38 |
| 37 | 7.60 | 2.00 | 6667 | 400 | 58.27 | 9.76 |
| 38 | 7.60 | 3.00 | 10,000 | 400 | 36.24 | 12.93 |
| 39 | 7.60 | 4.00 | 13,333 | 400 | 49.52 | 10.42 |

All examples in Table 5 were at 1000 psig with a molar ratio of hydrogen:carbon monoxide of 1:1 and 18 ml of catalyst. Results show that conversion of methanol to higher alcohols varies only slightly with gas flow rate over the range 1300 to 13000 v/v/hour.

Further examples using alkali metal containing uranium catalysts are summarized in Table 6 below. The catalyst employed in Examples 40 to 44 was that prepared in Preparation E (pelletized).

TABLE 6
Methanol Homologation Over Cesium Doped Uranium Catalyst

| Example No. | MeOH Feed Rate g/hr | Gas Hourly Space Velocity V/V/Hour | H$_2$:CO Molar Ratio | Temp. °C. | % MeOH Conv. | % MeOH Conv. to Higher Alcs. |
|---|---|---|---|---|---|---|
| 40 | 10.446 | 2400 | 1.0 | 350 | 22.0 | 5.30 |
| 41 | 10.446 | 2400 | 1.0 | 375 | 43.0 | 8.21 |
| 42 | 10.446 | 2400 | 1.0 | 400 | 63.4 | 13.07 |
| 43 | 10.446 | 6000 | 1.0 | 400 | 55.4 | 15.77 |
| 44 | 10.446 | 7200 | 0.2 | 425 | 94.8 | 18.34 |

In all of Examples 40–44 the pressure was 1000 psig.

In all the above Tables the term higher alcohols refers to alcohols containing two or more carbon atoms.

EXAMPLES 45 AND 46

Conversion of a Mixture of Methanol and Ethanol

A 10 ml portion of the catalyst of Preparation F was charged to the reactor. A solution with a 1:1 molar ratio of methanol:ethanol was passed over the catalyst at a rate of 9.6 ml/hour. In Example 45 nitrogen was fed to the catalyst as a carrier at a rate of 0.30 SLPM and the reactor was heated to 400° C. In Example 46 a synthesis gas with a 2:1 molar ratio of hydrogen:carbon monoxide was fed as coreactant at 1.50 SLPM. The results are recorded in Table 7.

TABLE 7

| Example | Temp. Gas | °C. | % Conversion of Methanol* | % Conversion of Ethanol** | % Conversion of Methanol*** and Ethanol to Higher Alcohols |
|---|---|---|---|---|---|
| 45 | Nitrogen | 400 | 30.7 | 73.5 | 5.65 |
| 46 | H$_2$/CO | 400 | 47.4 | 81.9 | 11.92 |

Pressure 750 psig

*$100 \times \frac{\text{(moles methanol fed} - \text{moles methanol recovered)}}{\text{moles methanol fed}}$

**$100 \times \frac{\text{(moles ethanol fed} - \text{moles ethanol recovered)}}{\text{moles ethanol fed}}$

***$100 \times \frac{\text{moles carbon in C}_2 + \text{alcohols}}{\text{moles carbon in methanol and ethanol fed}}$ Example 45 is included for comparative purposes and when compared with Example 46 demonstrates the improved conversion of methanol and ethanol to alcohols containing at least three carbon atoms in the presence of synthesis gas.

Preparation H: Catalyst Containing Chromium Oxide and Cesium 461.8 g of Cr(NO$_3$)$_3$.9H$_2$O (1.15 moles) were dissolved in 1 liter of distilled water and heated to 82° C. with stirring. A 2M solution of potassium carbonate warmed to 80° C. was added dropwise to the nitrate solution until the pH reached 7 at which point the solution was green-blue in color and very viscous. The mixture was filtered and the filter cake suspended in 1500 ml of distilled water and heated to 80° C. with stirring, maintained at 80° C. for 15 minutes and then filtered. The filter cake was resuspended in 1500 ml of distilled water again heated to 80° C. maintained for 15 minutes and filtered. The filter cake was dried in an oven at 120° C. overnight and calcined in air as follows: the temperature was raised from 20° C. to 400° C. at 1° C. per minute and then held at 400° C. for two hours and slowly allowed to cool to room temperature.

30.09 g of the above catalyst was impregnated with a solution of 2.96 g of cesium hydroxide dissolved in 10 ml of distilled water and dried in an oven at 120° C. for two hours. The thus prepared cesium doped chromium oxide catalyst contained 7.1% cesium by weight.

COMPARATIVE EXAMPLES 1-3

10 ml (17.72 g) of the catalyst from Preparation H was charged to the reactor. A synthesis gas of 1:1 molar ratio of hydrogen to carbon monoxide was fed. In each case the pressure was 1000 psig and the feed ratio was 4800 liters/liter/hour of gas and 0.5-1.0 cc/cc/hour of liquids. Three runs each of one hour were performed at 350° C., 375° C. and 400° C. respectively. The results are summarized in Table 8.

Preparation I: Catalyst Containing Molybdenum Oxide and Cesium 500.2 g of (NH$_4$)$_6$Mo$_7$O$_{24}$.4H$_2$O (0.405 mole) was dissolved in about 1500 ml of distilled water and 2M nitric acid was added dropwise. A white precipitate formed when the pH reached 3 and the mixture was filtered. The filter cake was resuspended in 1500 ml of distilled water and stirred for 20 minutes and filtered again. The filter cake was dried overnight in an oven at 120° C. and then calcined as follows: temperature raised 20° C. to 200° C. at 1° C. per minute then held at 200° C. for two hours, then raised 200° C. to 250° C. at 1° C. per minute and held at 250° C. for one hour and allowed to gradually cool at room temperature. The heated filter cake was then calcined at 400° C. for two hours. The color changed from a greenish tinged white to olive green. 35.09 g of the above prepared MoO$_x$ was impregnated with a solution of 3.41 g of cesium hydroxide in 8 ml of distilled water and then dried in air at 120° C. for two hours.

The thus prepared catalyst contained 7.01% by weight of cesium.

COMPARATIVE EXAMPLES 4 AND 5

10 ml (14.09 g) of the thus prepared catalyst from Preparation I was charged to the reactor. A synthesis gas of 1:1 molar ratio of hydrogen to carbon monoxide was fed. In each of two runs the pressure was 1000 psig and the feed rate was 4800 liters/liter/hour and 0.5 to 1.0 g/cc/hour of liquid feed. Two runs were performed, each of one hour at 350° C. and 375° C. respectively. The results are shown in Table 8.

TABLE 8

Chromium Oxide and Molybdenum Oxide Catalysts

| Catalyst | Comparative Example | Temp. °C. | % Conversion of Methanol | % Conversion of Methanol to Higher Alcohols |
|---|---|---|---|---|
| CrO$_3$ 7% Cs | 1 | 350 | 6.9 | 0.08 |
|  | 2 | 375 | 14.1 | 0.35 |
|  | 3 | 400 | 18.2 | 1.4 |
| MoO$_x$ 7% Cs | 4 | 350 | 100 | none |
|  | 5 | 375 | 100 | none |

Comparative Examples 1 to 5 with chromium oxide and molybdenum oxide catalysts when compared with Examples 14–16 in Table 1 and 40–44 in Table 6 demonstrate that uranium and thorium catalysts give a higher % conversion of methanol to higher alcohols. The different space velocities used with the two groups of catalysts do not significantly contribute to the different results since, as has been shown in Table 5 the conversion of methanol to higher alcohols varies only slightly over the range 1300 to 13,000 v/v/hour.

Preparation J: Catalyst Containing Thorium, Zinc and Potassium 100 g of Th(NO$_3$)$_4$.4H$_2$O (0.18 Moles) and 80.84 g Zn(NO$_3$)$_2$.6H$_2$O (0.27 Moles) were added to 2.5 liters distilled water and the solution was heated to about 95° C. A 2 Molar K$_2$CO$_3$ solution was then added dropwise with vigorous stirring. At pH about 3.5 a gelatinous precipitate began to form. The K$_2$CO$_3$ solution was added until the pH reached about 8.0. 2 Molar HNO$_3$ was then added to bring the pH back to 7.0. The mixture was digested hot for about one hour, then filtered. The moist filter cake was reslurried in one liter distilled H$_2$O, heated to 60° C., stirred for 30 minutes, then filtered. This process was repeated 2 more times. The dried filter cake was then dried overnight at 110° C. The powder was then calcined at 400° C. for 4 hours.

The thus prepared catalyst contained:
Th 57%,
K 1%,
Zn 23%,
corresponding to a formula of ThZn$_{1.43}$K$_{0.11}$O$_x$.

EXAMPLES 47 AND 48

The catalyst of Preparation J was employed at 1000 psig with a synthesis gas of molar ratio 1:1 carbon monoxide:hydrogen at a space velocity of 2400 liters/liter/hour. The results are recorded in Table 9.

TABLE 9

| Comparative Example | MeOH Feed Ratio g/hour | Temperature °C. | % MeOH Converted | % MeOH Converted to Higher Alcohols |
|---|---|---|---|---|
| 47 | 9.18 | 350 | 88.0 | 1.24 |
| 48 | 10.45 | 375 | 96.9 | 3.58 |

The above examples demonstrate that the presence of the hydrogenating metal namely zinc reduces the effectiveness of the catalyst.

We claim:

1. A process for the conversion of methanol to alcohols containing at least two carbon atoms which process comprises reacting methanol with carbon monoxide and/or hydrogen at elevated temperature and superatmospheric pressure in the presence, of a catalyst consisting of (i) an oxide of Th and/or U and (ii) one or more alkali metals the latter being present in an amount of at least 1% by weight of alkali metal based on the total weight of the oxide and alkali metal.

2. The process as claimed in claim 1 wherein the alkali metal is present in an amount from 3 to 20% by weight.

3. The process as claimed in claim 1 wherein the alkali metal is potassium.

4. The process as claimed in claim 1 wherein the alkali metal is cesium.

5. The process as claimed in claim 1 wherein the temperature is from 100° to 600° C. and the pressure from 10 to 2500 psig.

6. The process as claimed in claim 4 wherein the temperature is from 250° to 500° C. and the pressure from 50 to 2000 psig.

7. The process as claimed in claim 1 wherein the carbon monoxide and/or hydrogen is provided at least in part by recycling the product gases from the reaction.

8. The process as claimed in claim 1 wherein the methanol and carbon monoxide and/or hydrogen is obtained by reacting synthesis gas at elevated temperature and pressure in the presence of a methanol-forming catalyst.

9. The process as claimed in claim 1 wherein ethanol is passed with the methanol to the reaction and alcohols containing more than 2 carbon atoms recovered.

10. A process for the conversion of methanol to alcohols containing at least two carbon atoms which process comprises reacting methanol at elevated temperature and pressure with at least one gas selected from the group consisting of carbon monoxide and hydrogen in the presence of a cataysts consisting of an oxide of a metal selected from the group consisting of Th and U.

11. The process as claimed in claim 10 wherein the catalyst contains an alkali metal present in an amount of at least 1% by weight of alkali metal based on the total weight of oxide and alkali metal.

12. The process as claimed in claim 11 wherein the alkali metal is present is an amount from 3 to 20% by weight.

13. The process as claimed in claim 11 wherein the alkali metal is cesium.

14. The process as claimed in claim 10 wherein the temperature is from 100° to 600° C. and the pressure from 10 to 2500 psig.

15. The process as claimed in claim 14 wherein the temperature is from 250° to 500° C. and the pressure from 50 to 2000 psig.

16. The process as claimed in claim 10 wherein the carbon monoxide and/or hydrogen is provided at least in part by recycling the product gases from the reactor.

17. The process as claimed in claim 10 wherein ethanol is passed with the methanol to the reaction and alcohols containing more than 2 atoms recovered.

* * * * *